United States Patent
Kim et al.

(10) Patent No.: US 10,363,262 B1
(45) Date of Patent: Jul. 30, 2019

(54) COMPOSITION FOR TREATING WOUND COMPRISING GYPENOSIDE LXXV

(71) Applicant: Intelligent Synthetic Biology Center, Daejeon (KR)

(72) Inventors: Sun-Chang Kim, Daejeon (KR); Sungjoo Park, Incheon (KR); Eun Su Ko, Gyeonggi-do (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 0 days.

(21) Appl. No.: 16/191,312

(22) Filed: Nov. 14, 2018

(30) Foreign Application Priority Data

Oct. 22, 2018 (KR) ........................ 10-2018-0125961

(51) Int. Cl.
| | |
|---|---|
| *A61K 31/7028* | (2006.01) |
| *A61K 9/00* | (2006.01) |
| *A61P 17/02* | (2006.01) |
| *A61K 9/12* | (2006.01) |
| *A61K 9/06* | (2006.01) |

(52) U.S. Cl.
CPC ........ *A61K 31/7028* (2013.01); *A61K 9/0014* (2013.01); *A61K 9/06* (2013.01); *A61K 9/12* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 2018/0140623 A1* | 5/2018 | Cui | ........................ A23L 33/10 |
| 2018/0228823 A1* | 8/2018 | Kim | ..................... A23K 20/163 |

OTHER PUBLICATIONS

Gonzalez et al., "Wound healing—literature review", An Bras Dermatol., 2016, 91(5), 614-20.
Grazul-Bilska et al., "Wound Healing: The Role of Growth Factors", Drugs of Today, 2003, 39(10), 787-800.
Shibata, Shoji, Chemistry and Cancer Preventing Activities of Ginseng Saponins and Some Related Triterpenoid Compounds, J. Korean Med sci, 2001, 16(Suppl), S28-37.
Sorg et al., "Skin Wound Healing: An Update on the Current Knowledge and Concepts", Eur Surg Res, 2017, 58, 81-94.

* cited by examiner

*Primary Examiner* — Traviss C McIntosh, III
(74) *Attorney, Agent, or Firm* — Gavrilovich, Dodd & Lindsey LLP (57) ABSTRACT

The present invention relates to a composition for wound healing or skin regeneration comprising gypenoside 75 (gypenoside LXXV) as an active ingredient.

8 Claims, 5 Drawing Sheets

COMPOSITION FOR TREATING WOUND COMPRISING GYPENOSIDE LXXV

CROSS REFERENCE TO RELATED APPLICATIONS

This Application claims priority under 35 U.S.C. § 119 to Korean Application No. 10-2018-0125961, filed Oct. 22, 2018, the disclosure of which is incorporated herein by reference.

TECHNICAL FIELD

The present invention relates to a composition for wound healing or skin regeneration containing gypenoside LXXV (gypenoside 75) as an active ingredient.

BACKGROUND ART

Skin, which is the body's first line of defense against disease, acts as a protective barrier for the body, and the epidermis serves as a barrier against invading microorganisms. Accordingly, the primary purpose in the treatment of cuts, burns, abrasions, and other injuries to the skin, which are also referred to as wounds, is rapid closure and wound healing to prevent infection.

Wound healing clinically means that the skin is completely closed, and it is a complex process controlled by the interaction of many kinds of cells (e.g., keratinocytes, fibroblasts, endothelial cells, macrophages, platelets, etc.) (Sorg et al., *European Surgical Research*, 2017; Gonzalez et al., *An Bras Dermato*, 2016). Each process is controlled by a complex signaling network regulated by many growth factors, cytokines, and chemokines.

In general, wound healing is a complex process which occurs in three stages (i.e., inflammation, proliferation, and remodeling) (Grazul-Bilska et al., *Drugs of Today* 39, 2003). The first stage involves clotting to achieve hemostasis, supplementation of neutrophils to destroy bacteria and necrotic tissue, and subsequent supplementation of macrophages. During the second stage, angiogenesis occurs, and the endothelial cells enter the wound site, and simultaneously, fibroblasts enter the wound site and help to produce granulation tissue. The formation of granulation tissue causes re-epithelialization to occur. During the final stage, the levels of collagen production and destruction equalize, and the wound healed slowly changes to achieve maximum strength. Wound healing is delayed or damaged when any one of these stages does not function properly or in a timely manner. This can cause the wound to become a chronic wound, which is not only important to individuals but also can be a costly clinical problem. Accordingly, compositions that can accelerate the natural processes of the body that regenerate the skin and epidermal tissue are needed.

Meanwhile, *ginseng* contains various kinds of ginsenosides (e.g., panaxadiol ginsenosides (PD), panaxatriol ginsenosides (PT), oleanane ginsenosides, etc.) and gypenosides. The functions of ginsenosides (e.g., enhancement of immune function, excitatory action in the central nervous system, stimulation of secretion of adrenocorticotropic hormone, inhibition of platelet aggregation, etc.) vary depending on the kind, and thus, it is difficult to predict whether a ginsenoside of the same kind may have the same effect.

Under the circumstances, the present inventors have confirmed that gypenoside 75 (gypenoside LXXV) is involved in the migration and proliferation of keratinocytes and exhibits a wound healing effect in a mouse model, thereby completing the present invention.

DISCLOSURE

Technical Problem

An object of the present invention is to provide a pharmaceutical composition for wound healing or skin regeneration containing gypenoside 75 (gypenoside LXXV) as an active ingredient.

Another object of the present invention is to provide a quasi-drug composition for wound healing or skin regeneration containing gypenoside 75 (gypenoside LXXV) as an active ingredient.

Still another object of the present invention is to provide a cosmetic composition for skin moisturization containing gypenoside 75 (gypenoside LXXV) as an active ingredient.

Technical Solution

The preferred embodiments are described in detail as follows. Meanwhile, respective descriptions and embodiments disclosed in the present invention may also be applied to other descriptions and embodiments. That is, all combinations of various elements disclosed in the present invention fall within the scope of the present invention. Further, the scope of the present invention is not limited by the specific description below.

In addition, those skilled in the art can recognize or confirm a plurality of equivalents to the specific aspects of the invention described herein based only on conventional experimentation. Further, such equivalents are intended to be included in the present invention.

To achieve the above objects, an aspect of the present invention provides a pharmaceutical composition for wound healing or skin regeneration containing gypenoside 75 (gypenoside LXXV) as an active ingredient.

As used herein, the term "gypenoside LXXV" may be used interchangeably with "gypenoside 75", "GypLXXV", and "G75". Specifically, gypenoside LXXV may be represented by Formula 1.

Formula I

The gypenoside LXXV can be chemically synthesized or separated from natural materials. When the gypenoside LXXV of the present invention is separated from a natural substance, it may be a concept that includes both an extract of a natural product or a fraction thereof as long as it includes the gypenoside LXXV.

Additionally, the compound according to the present invention may have an asymmetric carbon center and thus it may exist as R or S isomers, racemates, diastereomer mixtures, and individual diastereomers, and all of these isomers and mixtures are included within the scope of the present invention.

As used herein, the term "gypenoside (Gyp)" refers to a triterpenoid saponin. Known examples of the gypenoside include GypXVII, GypXLIX, GypLXXIV, GypXLV, gypenoside UL1, gypenoside UL2, gypenoside UL3, gypenoside UL4, gypenoside UL5, gypenoside UL6, gypenoside UL7, etc. in addition to GypLXXV.

The gypenoside LXXV of the present invention may be obtained by deglycosylation of ginsenoside Rb1 according to a known method or a commercially available gypenoside LXXV may be purchased and used.

As used herein, the term "deglycosylation" refers to the removal of a glycoside from a compound to which it is bound. The term "glycoside" refers to a molecule in which a sugar is bound to another functional group via a glycosidic bond. For the purposes of the present invention, the deglycosylation means that the glycoside in a ginsenoside compound is removed by hydrolysis, and the glycoside may be interpreted to have the same meaning as a glucose moiety. Generally, the effects of ginsenosides are known to increase with the degree of deglycosylation enhancing hydrophobicity and cell wall permeability of these ginsenosides (Shibata S., 2001, *J. Korean Med. Sci.*, 16 Suppl: S28-37), and the GypLXXV of the present invention obtained by deglycosylation from ginsenoside Rb1 is also known to have a greater in vivo absorption rate than ginsenosides having a large size (about 1,000 Da).

As used herein, the term "wound healing" refers to the treatment of a wound due to skin cell damage, in which the term wound has a meaning to cover all kinds of in vivo injuries of the body. The term "treatment" may refer to all activities that inhibit or delay the worsening of the wound, or to ameliorate or advantageously change the symptoms of the wound by administering the pharmaceutical composition of the present invention to a subject with a wound.

The term "subject" may refer to all animals, including humans, in which a wound has occurred or may be able to occur. The animal may be a mammal, such as cows, horses, sheep, pigs, goats, camels, antelopes, dogs, cats, etc. as well as humans, that require treatment for similar symptoms, but the animal is not limited thereto.

As used herein, the term "skin regeneration" collectively refers to all of the increase of skin moisturization, improvement of skin elasticity, increase of skin thickness, improvement of skin wrinkles, alleviation of skin irritation, and recovery of skin damage, and specifically refers to regeneration of the skin from the damage caused by physical factors, but skin regeneration is not limited thereto.

The composition may be characterized in that it mediates proliferation or migration of skin fibroblasts or keratinocytes.

In an embodiment of the present invention, it was confirmed that gypenoside LXXV promotes proliferation and migration of keratinocytes (HaCaT cells) and human dermal fibroblasts, which is known to have an important role in wound healing. As a result, it was confirmed that gypenoside LXXV is superior to the control group with respect to proliferation and migration of cells, and this implies that the composition of the present invention may be used for wound healing or skin regeneration. Additionally, the composition of the present invention may be used for promoting in vitro proliferation and migration of cells, but the use of the composition is not limited thereto. Additionally, the skin cells may include keratinocytes and human dermal fibroblasts, but the skin cells are not limited thereto.

The composition may be characterized in that it promotes the expression of growth factor genes.

In an embodiment of the present invention, the treatment of gypenoside LXXV on keratinocytes and skin fibroblasts promoted the expression of various kinds of genes (in particular growth factor genes), and thus it was confirmed that gypenoside LXXV is involved in skin regeneration, and this implies that the composition of the present invention may be used for wound healing or skin regeneration.

The amount of the gypenoside LXXV to be contained in the pharmaceutical composition of the present invention may not be limited as long as the pharmaceutical composition shows an effect of wound healing or skin regeneration, and the gypenoside LXXV may be contained in an amount of 0.0001 wt % to 50 wt % relative to the total weight of the final composition, and specifically 0.01 wt % to 10 wt %.

The composition may further include a pharmaceutically acceptable carrier.

As used herein, the term "pharmaceutically acceptable" refers to a feature of being non-toxic to a cell or human exposed to the composition.

Specifically, the pharmaceutical composition may be formulated in oral dosage forms, including powders, granules, tablets, capsules, suspensions, emulsions, syrup, aerosol, etc.; preparations for external application; suppositories; and sterile injectable solutions. In the present invention, the carriers, excipients, and diluents that may be included in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition of the present invention may be formulated with commonly used diluents or excipients (e.g., fillers, extenders, binders, wetting agents, disintegrants, surfactants, etc.). Solid formulations for oral administration may include tablets, pills, powders, granules, capsules, etc., and such solid formulations may be prepared by mixing with at least one excipient (e.g., starch, calcium carbonate, sucrose, lactose, gelatin, etc.). In addition to simple excipients, lubricants (e.g., magnesium stearate or talc) may also be used. Liquid formulations for oral administration may include suspensions, solutions for internal use, emulsions, syrup, etc., and may include various excipients (e.g., wetting agents, flavoring agents, aromatics, preservatives, etc.), in addition to water and liquid paraffin, which are frequently used simple diluents. Formulations for parenteral administration may include sterilized aqueous solutions, non-aqueous solutions, suspensions, emulsions, lyophilized preparations, and suppositories. As non-aqueous solvents or suspending agents, propylene glycol, polyethylene glycol, plant oils (e.g., olive oil), injectable esters (e.g., ethyl oleate, etc.), etc. may be used. As the base of the suppositories, witepsol, Macrogol, Tween 61, cacao butter, laurin butter, glycerogelatin, etc. may be used. However, the composition of the present invention may be provided in the form of an external skin preparation, and specifically, in the form of an external skin preparation, such as a liquid preparation, an ointment preparation, a cream preparation, a lotion preparation, a spray preparation, a patch preparation, a gel preparation, or an aerosol preparation.

The pharmaceutical composition of the present invention may further include compounds commonly used in wound healing (e.g., antibiotics, anti-inflammatory agents, skin treatment formulations, anesthetics, analgesics, etc. These agents may vary slightly depending on each formulation, and may be included in the form of an external skin preparation, but these agents are not limited thereto. Generally, antibiotics, antimicrobial agents, etc. may be supplied to the wound area to prevent infection at the wound site or prevent worsening of the wound due to infection, and in addition, local anesthetics and analgesics may be supplied to alleviate pain; and anti-inflammatory agents (e.g., antihistamines) may be supplied to prevent excessive inflammatory reactions in wound healing. It is possible to promote convenience in use by supplying agents where various functional drugs are contained and to further improve the effects of these agents in wound healing by creating an environment that can be helpful for more efficient wound healing.

Another aspect of the present invention provides a method for wound healing by administering the composition to a subject in which a wound has occurred.

The pharmaceutical composition of the present invention may be administered in a pharmaceutically effective amount. As used herein, the term "pharmaceutically effective amount" refers to an amount which is sufficient to treat diseases at a reasonable benefit/risk ratio applicable to any medical treatment and does not cause any adverse effect. The effective dosage level may be readily determined by those skilled in the art, depending on factors including the patient's health conditions, the kind and severity of the wound, activity of the drug, drug sensitivity, administration method, administration time, administration route and excretion rate, duration of treatment, the drugs used in combination or used concurrently, and other factors well known in the medical field.

As used herein, the term "administration" refers to the introduction of a predetermined material into a subject by any suitable method.

In the method for wound healing of the present invention, the route and method of administration of the composition are not particularly limited, and any route and method of administration by which the composition can reach the corresponding target region may be used. Specifically, the composition may be administered via various routes including oral or parenteral routes. Non-limiting examples of the administration routes may include an oral, rectal, topical, intravenous, intraperitoneal, intramuscular, intraarterial, transdermal, intranasal, or inhalation route, etc., and more specifically the composition may be administered by applying to the skin, but the administration route is not limited thereto.

Still another aspect of the present invention provides a quasi-drug composition for wound healing or skin regeneration containing gypenoside LXXV as an active ingredient.

As used herein, the term "quasi-drug" refers to a product which falls under any of the following: (a) fiber or rubber products or analogs thereof which are used for the curing, alleviation, treatment, or prevention of disease in humans or animals; (b) products other than instruments and machines, and analogs thereof which have a weak action in humans or do not directly act upon the human body; (c) products corresponding to any of the germicides or insecticides, and analogs thereof for the prevention of epidemics, which are other than instruments, machines, and apparatus that are used for the diagnosis, cure, alleviation, treatment, or prevention of disease in humans or animals; and (d) products excluding those other than instruments, machines, and apparatus among the products which are used for providing pharmacological effects on the structures and functions of humans or animals.

When the composition is used as an additive for a quasi-drug, the composition may be added as is or may be used together with other quasi-drugs or components of quasi-drugs, and may be appropriately used according to a conventional method. The amount of the active ingredient to be mixed may be appropriately determined depending on the purpose of use.

Specifically, the quasi-drug composition of the present invention may be a disinfectant cleaner, shower foam, oral cleanser, wet wipe, detergent soap, hand wash, humidifier filler, mask, ointment, filter filler, etc., but the quasi-drug composition is not limited thereto.

Still another aspect of the present invention provides a cosmetic composition for skin regeneration containing gypenoside LXXV as an active ingredient.

The cosmetic composition of the present invention shows effects of the improvement of skin wrinkles and wound healing as well as for skin regeneration, and these are already described above. The cosmetic composition may be produced in various forms according to a conventional method for preparing cosmetics. For example, the cosmetic composition may be prepared in the form of a perfume product, emollient, cream, lotion, etc. containing gypenosides, and it may be used after diluting with a conventional cleansing solution, astringent solution, and moisturizing solution. Additionally, the cosmetic composition may contain a conventional adjuvant (e.g., stabilizers, solubilizers, vitamins, pigments, and perfumes) commonly used in the cosmetic composition field. In the cosmetic composition, gypenosides may be contained in an effective amount to achieve skin regeneration and wound clearing, for example, in an amount of 0.001 wt % to 10 wt %, and specifically about 0.01 wt % to about 1 wt %, based on the total weight of the composition.

The cosmetic composition may be formulated in the form of a solution, ointment for external use, cream, foam, nutrition emollient, soft emollient, perfume, pack, soft water, emulsion, makeup base, essence, soap, liquid cleansing agent, bath preparation, sunscreen cream, sun oil, suspension, paste, gel, lotion, powder, surfactant-containing cleansing agent, oil, powder foundation, emulsion foundation, wax foundation, patch, and spray, but the formulation is not limited thereto.

The cosmetic composition may further contain at least one kind of a cosmetically acceptable carrier to be incorporated into the common skin cosmetics. As a conventional component of the cosmetically acceptable carrier, for example, an oil fraction, water, surfactant, moisturizing agent, lower alcohol, thickener, chelating agent, inorganic salt, pigment, antioxidant, bactericide, preservative, fragrance, etc. may be appropriately mixed, but the component is not limited thereto.

Advantageous Effects of the Invention

The composition of the present invention containing gypenoside LXXV as an active ingredient has excellent effects of wound healing and skin regeneration, and thus it can be used as a composition for wound healing and skin regeneration.

BRIEF DESCRIPTION OF DRAWINGS

FIG. 1A-B shows the experimental results with regard to the treatment of HaCaT keratinocytes with various kinds of ginsenosides at various concentrations, in which

FIG. 2A-C shows in vitro experimental data for gypenoside LXXV (G75) and madecassoside (MA), in which

FIG. 3A-B shows the experimental results for gypenoside LXXV (G75) and madecassoside (MA), in which

DETAILED DESCRIPTION OF THE INVENTION

Hereinafter, the present invention will be described in more detail with reference to the following Examples. However, these Examples are for illustrative purposes only and the scope of the invention is not limited by these Examples.

Example 1: Selection of *Ginseng* Components Effective in Wound Healing

Experiments were performed to examine the effects of various kinds of ginsenosides on migration and cell proliferation of HaCaT keratinocytes, which are important processes for wound healing.

Example 1-1: Analysis of Proliferation of HaCaT Keratinocytes

Figure 1A:
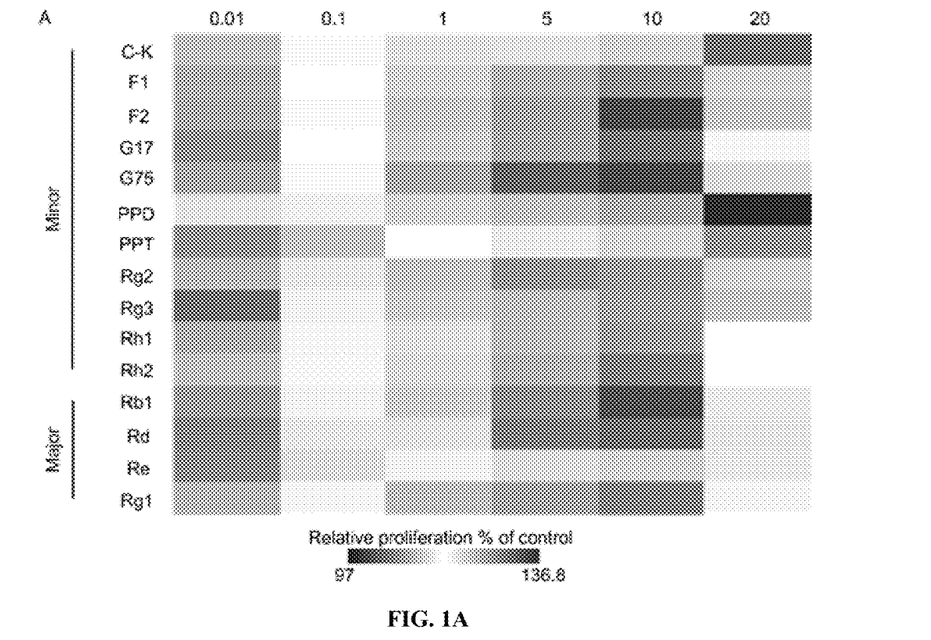
FIG. 1A shows the results of MTT analysis, wherein as the color becomes closer to blue, the relative proliferation value becomes lower, whereas as the color becomes closer to red, the relative proliferation value becomes greater.

HaCaT keratinocytes were treated with major ginsenosides (e.g., Rb1, Rd, Re, and Rg1) and other ginsenosides (e.g., C-K, F1, F2, G17, G75, PPD, PPT, Rg2, Rg3, Rh1, and Rh2) at a concentration of 0.01 μM to 20 μM for 48 hours and then subjected to MTT analysis (FIG. 1A). As the control group, DMSO was used.

As a result, it was confirmed that various kinds of ginsenosides showed effects on cell proliferation to some extent. Specifically, in most ginsenosides, the highest cell proliferation effect was shown when the ginsenoside concentration was at 10 μM, while the effect was actually reduced when the ginsenoside concentration was at 20 μM.

Additionally, most ginsenosides showed the cell proliferation effect by about 102% to about 120% relative to the control group, whereas G75 showed the cell proliferation effect by about 136.8%.

Example 1-2: Analysis of Migration of HaCaT Keratinocytes

The wound healing effects of G75 selected in Example 1-1 were examined by the scratch wound closure assay.

Figure 1B:
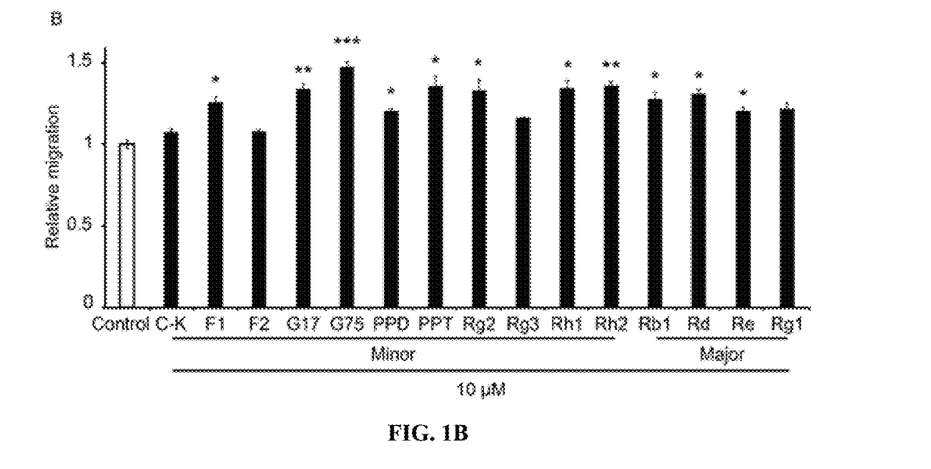
FIG. 1B shows a graph confirming the migration of HaCaT keratinocytes by phase-contrast microscopy.

Specifically, HaCaT keratinocytes were cultured in a 6-well plate and the plate was scratched using a 200 μL micropipette tip. The remainder was washed with PBS and the cells were cultured for 24 hours, treated with 10 μM ginsenoside or DMSO, and the gap regions were measured (FIG. 1B).

As a result, it was confirmed that most ginsenosides showed effects to some extent compared to the control group, and the cells treated with G75 showed the highest migration effect.

In conclusion, compared to other ginsenosides, G75 showed the highest cell proliferation effect on HaCaT keratinocytes, and the most significant cell proliferation effect was shown at a concentration of 10 μM.

Example 2: Wound Healing Effect of Gypenoside LXXV

Based on the results of Example 1, a comparative experiment was performed with regard to G75 and madecassoside (MA), a material known to be effective in wound healing.

Example 2-1: Confirmation of In Vitro Effect of Gypenoside LXXV

An in vitro experiment was performed using HaCaT keratinocytes and human dermal fibroblasts.

Figure 2A:
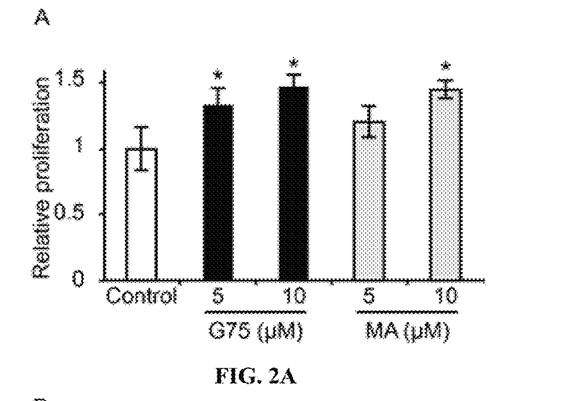
FIG. 2A shows a graph illustrating the cell proliferation of HaCaT keratinocytes and FIG. 2B shows a graph illustrating the cell proliferation of human dermal fibroblasts, both confirmed by MTT analysis.
Figure 2B:
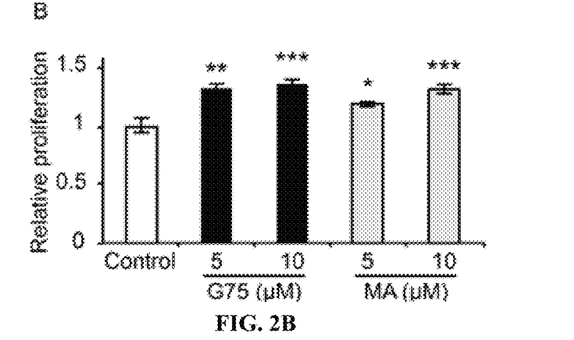
Figure 2C:
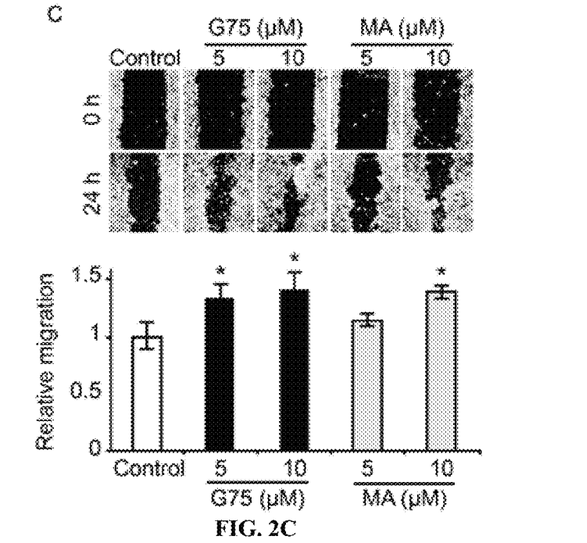
FIG. 2C shows a graph illustrating the migration of HaCaT keratinocytes by G75.
Figure 3A:
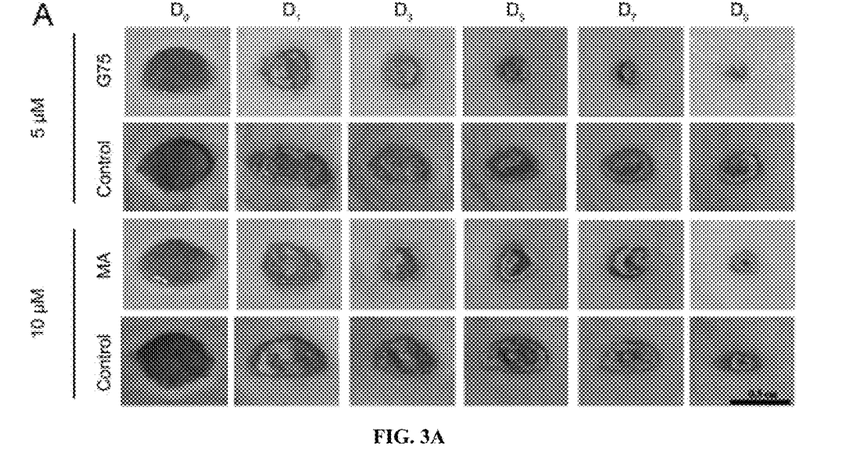
FIG. 3A shows images confirming their wound healing effect in mice.
Figure 3B:
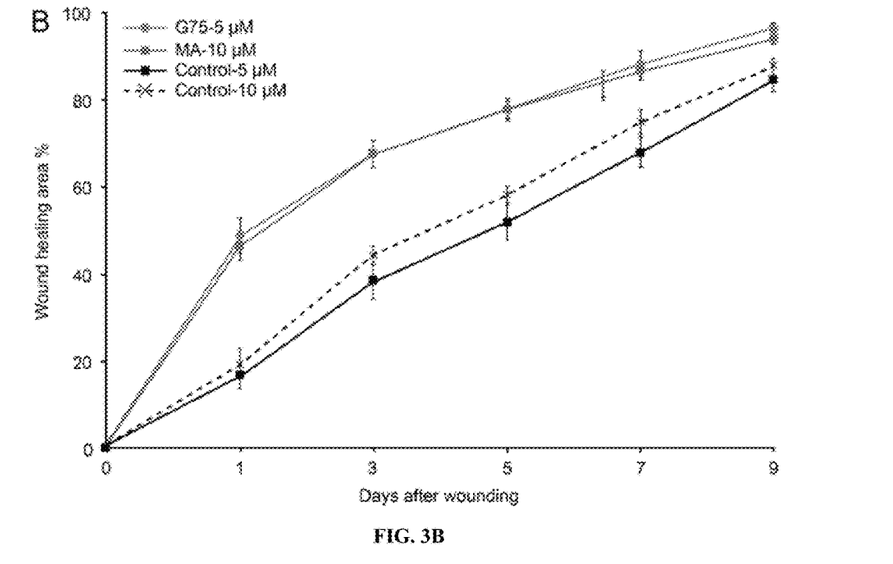
FIG. 3B shows a graph illustrating the wound healing area measured.
Figure 4:
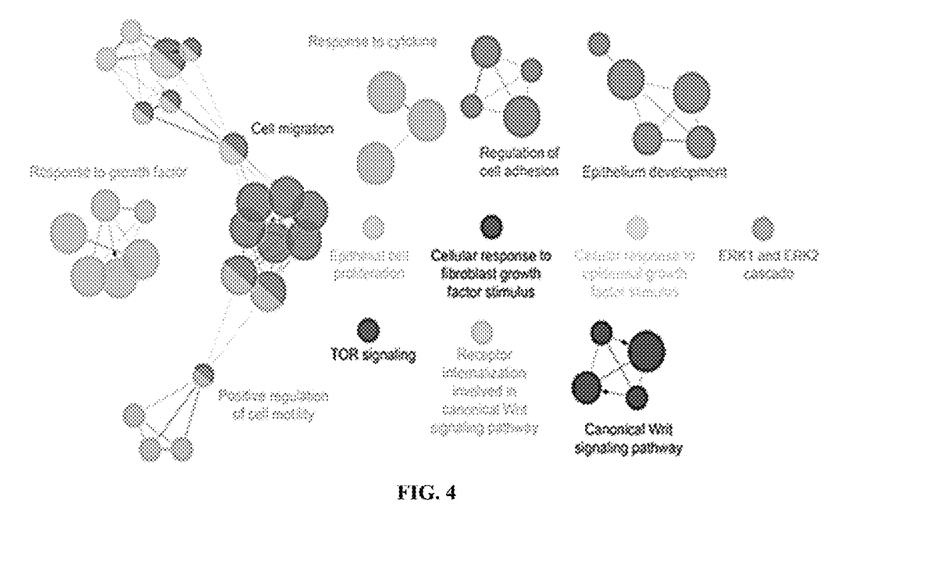
FIG. 4 shows a schematic diagram illustrating the correlation between the biological pathway involved in wound healing and gypenoside LXXV (G75).

Each cell was seeded into a 96-well plate and cultured at 37° C. for 48 hours. The cultured cells were treated with G75, MA, or DMSO at a concentration of 5 μM or 10 μM. After 48 hours, the proliferation of these cells was confirmed using the non-radioactive cell proliferation assay kit (Promega, WI, USA), and migration of these cells was confirmed in the same manner as in Example 1-2 (FIG. 2).

As a result, the MA treatment at 10 μM showed a slight effect in both types of cells, whereas the G75 treatment at both 5 μM and 10 μM showed a significant effect in cell proliferation and cell migration. Additionally, it was confirmed that G75 showed superior effects to MA at the same concentration.

Example 2-2: Confirmation of In Vivo Effect of Gypenoside LXXV

The in vivo wound closure activity was measured in an excision wound mouse model.

Eight-week-old male ICR mice were purchased from Narabiotech (Korea), acclimatized for one week, and used in the experiment. Two full-thickness circular wounds (diameter: 5 mm) were created on the dorsal region of each mouse, and the progressive changes in wound closure were measured relative to the original wound area. G75 (5 μM/wound) or MA (10 μM/wound) was then applied on each wound area once a day for 9 days. DMSO-propylene glycol was used as a vehicle control.

As a result, it was confirmed that the wound areas became smaller when treated with G75 or MA compared to those treated with the vehicle control, and these results were shown to be distinct from the following day after the treatment. Additionally, the treatment with G75 or MA generally showed a similar effect, or the G75 treatment tended to show a slightly better effect than the MA treatment.

In conclusion, it was confirmed that the treatment effect of G75 was similar to or better than that of madecassoside, a material known to be effective in wound healing, thus suggesting that the G75 of the present invention can be used in the composition for wound healing.

Example 3: Confirmation of Mechanism of Action of Gypenoside LXXV

To examine the process of G75 involvement in wound recovery, RNA sequencing was performed. After creating an excision wound on the dorsal area of each mouse, the wound was treated with G75 or the vehicle control, and RNA was isolated from the dorsal excisional wound tissue on the third day after the treatment and analyzed. When the p value was 0.05 or below and there was a change of 1.7-fold or greater, the change was considered to significant.

As a result, it was confirmed that the expression level of 1048 genes was changed by the G75 treatment, and these genes were predicted to regulate the expression of growth factors involved in wound healing.

To confirm the effect of G75 on the growth factors involved in wound healing, the mRNA levels of growth factors were measured based on the results of RNA sequencing analysis. The list of the growth factor genes whose expression level was significantly increased by G75 is shown in Table 1 below.

TABLE 1

| Growth Factors | Fold change | p-value |
|---|---|---|
| Fgf2 | 8.143 | 0.311 |
| Csf2 | 5.545 | 0.278 |
| CTGF | 1.879 | 0.022* |
| Angpt1 | 1.796 | 0.250 |
| Fgf7 | 1.789 | 0.070 |
| Fgf10 | 1.750 | 0.192 |
| Tgf alpha | 1.504 | 0.278 |
| Tgf beta1 | 1.392 | 0.199 |
| Igf1 | 1.367 | 0.974 |
| Vegf alpha | 1.281 | 0.343 |
| Hbegf | 1.267 | 0.685 |
| Hgf | 1.191 | 0.826 |

As a result, it was confirmed that the expression level of connective tissue growth factor (CTGF) was most significantly increased.

Figure 5A:
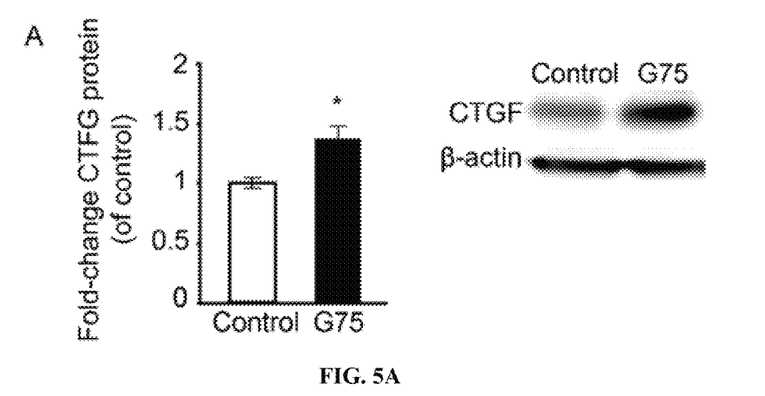
FIGS. 5A and 5B respectively show a graph illustrating the comparison results of CTGF protein expression level in the wound tissue treated with G75.
Figure 5B:
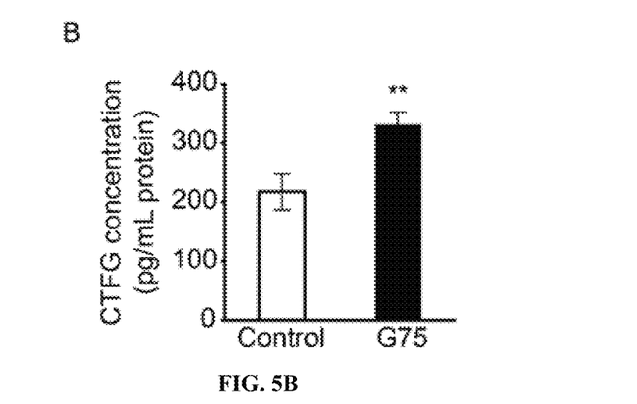

To examine whether the G75 treatment increases the expression level of CTGF protein, each wound was treated with G75, and after 3 days, the skin tissue was collected and subjected to western blot. As a result, it was confirmed that the expression level of CTGF protein was significantly increased (FIG. 5A). Additionally, as a result of ELISA assay, it was confirmed that the G75 treatment on the supernatant of human dermal fibroblasts increased the amount of CTGF production (FIG. 5B).

Figure 5C:
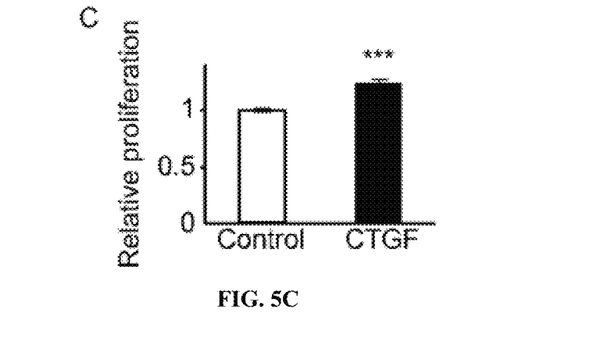
FIG. 5C shows a graph confirming the proliferation of human dermal fibroblasts in the wound tissue treated with CTGF.

Additionally, it was confirmed that when treated with CTGF, human dermal fibroblasts showed a higher level of proliferation compared to the vehicle control (FIG. 5C).

From the above experimental results, it was found that G75 is involved in the production of CTGF, thereby exhibiting a wound healing effect.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method of wound healing or skin regeneration, comprising administering a composition comprising gypenoside 75 (gypenoside LXXV).

2. The method of claim 1, wherein the composition mediates proliferation or migration of skin fibroblasts or keratinocytes.

3. The method of claim 1, wherein the composition promotes the expression of growth factor genes.

4. The method of claim 1, wherein the composition further comprises a pharmaceutically acceptable carrier.

5. The method of claim 1, wherein the composition is provided in the form of an external skin preparation.

6. The method of claim 1, wherein the composition is a liquid preparation, an ointment preparation, a cream preparation, a lotion preparation, a spray preparation, a patch preparation, a gel preparation, or an aerosol preparation.

7. The method of claim 1, wherein the composition is a quasi-drug composition or a cosmetic composition.

8. The method of claim 1, wherein the composition is a pharmaceutical composition.

* * * * *